United States Patent
Bertolero et al.

(10) Patent No.: US 10,098,640 B2
(45) Date of Patent: Oct. 16, 2018

(54) LEFT ATRIAL APPENDAGE DEVICES AND METHODS

(75) Inventors: Arthur A. Bertolero, Danville, CA (US); Tamer Ibrahim, Danville, CA (US); Steve Geyster, Milton, WA (US)

(73) Assignee: AtriCure, Inc., Mason, OH (US)

( * ) Notice: Subject to any disclaimer, the term of this patent is extended or adjusted under 35 U.S.C. 154(b) by 158 days.

(21) Appl. No.: 12/886,436

(22) Filed: Sep. 20, 2010

(65) Prior Publication Data

US 2011/0009853 A1 Jan. 13, 2011

Related U.S. Application Data

(60) Division of application No. 10/988,003, filed on Nov. 12, 2004, now abandoned, which is a continuation-in-part of application No. 10/310,675, filed on Dec. 4, 2002, now Pat. No. 7,749,157.

(60) Provisional application No. 60/519,359, filed on Nov. 11, 2003, provisional application No. 60/337,070, filed on Dec. 4, 2001.

(51) Int. Cl.
| | |
|---|---|
| *A61B 17/08* | (2006.01) |
| *A61B 17/10* | (2006.01) |
| *A61B 17/122* | (2006.01) |
| *A61B 17/128* | (2006.01) |
| *A61B 17/068* | (2006.01) |
| *A61B 17/00* | (2006.01) |
| *A61B 17/32* | (2006.01) |

(52) U.S. Cl.
CPC .......... *A61B 17/083* (2013.01); *A61B 17/068* (2013.01); *A61B 17/08* (2013.01); *A61B 17/122* (2013.01); *A61B 17/1285* (2013.01); *A61B 17/0057* (2013.01); *A61B 17/320016* (2013.01); *A61B 2017/00243* (2013.01)

(58) Field of Classification Search
CPC ............................ A61B 17/122; A61B 17/128
USPC ........................................................ 606/151
See application file for complete search history.

(56) References Cited

U.S. PATENT DOCUMENTS

| | | | |
|---|---|---|---|
| 2,060,724 A | 11/1936 | Carroll | |
| 2,371,978 A | 3/1945 | Perham | |
| 3,032,039 A | 5/1962 | Beaty | |

(Continued)

FOREIGN PATENT DOCUMENTS

| | | |
|---|---|---|
| AU | 2005202273 | 12/2002 |
| EP | 1600108 | 11/2005 |

(Continued)

OTHER PUBLICATIONS

Aydin Aytac MD et al., Intrapericardial Aneurysm of the Left Atrial Appendage Article, pp. 509-512, 1980.

(Continued)

*Primary Examiner* — Diane Yabut
(74) *Attorney, Agent, or Firm* — Levine Bagade Han LLP

(57) ABSTRACT

Devices and methods for clamping tissue and/or moving two tissue structures together by moving two plates or arm together. The pressure or force applied to the tissue may be used to bring the tissue together, to seal an opening or to cut through and remove a portion of the tissue. In one procedure disclosed, a clip applier may be used to apply one or more clips to the left atrial appendage of the heart to prevent clots from the left atrial appendage from embolizing and causing harm to the patient, such as a stroke.

25 Claims, 7 Drawing Sheets

(56) References Cited

U.S. PATENT DOCUMENTS

| | | | |
|---|---|---|---|
| 3,496,932 A | 2/1970 | Bert et al. | |
| 3,682,180 A | 8/1972 | McFarlane | |
| 3,726,279 A | 4/1973 | Barefoot et al. | |
| 3,777,336 A | 12/1973 | Anderson | |
| 3,783,873 A | 1/1974 | Jacobs | |
| 3,854,482 A | 12/1974 | Laugherty et al. | |
| 3,856,016 A | 12/1974 | Davis | |
| 3,856,017 A | 12/1974 | Perisse et al. | |
| 3,856,018 A | 12/1974 | Perisse et al. | |
| 3,954,108 A | 5/1976 | Davis | |
| 4,226,239 A | 10/1980 | Polk et al. | |
| 4,274,415 A | 6/1981 | Kanamoto et al. | |
| 4,493,319 A | 1/1985 | Polk et al. | |
| 4,552,128 A | 11/1985 | Haber | |
| 4,558,699 A | 12/1985 | Bashour | |
| 4,598,711 A | 7/1986 | Deniega | |
| 4,612,923 A | 9/1986 | Kronenthal | |
| 4,788,966 A | 12/1988 | Yoon | |
| 4,791,707 A | 12/1988 | Tucker | |
| 4,869,268 A | 9/1989 | Yoon | |
| 4,917,677 A | 4/1990 | McCarthy | |
| 4,950,284 A | 8/1990 | Green et al. | |
| 5,026,379 A | 6/1991 | Yoon | |
| 5,062,846 A * | 11/1991 | Oh et al. | 606/158 |
| 5,074,870 A | 12/1991 | Von Zeppelin | |
| 5,100,416 A | 3/1992 | Oh et al. | |
| 5,119,804 A | 6/1992 | Anstadt | |
| 5,160,339 A | 11/1992 | Chen et al. | |
| 5,171,250 A | 12/1992 | Yoon | |
| 5,203,786 A | 4/1993 | Vernick | |
| 5,217,030 A | 6/1993 | Yoon | |
| 5,217,473 A | 6/1993 | Yoon | |
| 5,222,961 A | 6/1993 | Nakao et al. | |
| 5,258,000 A | 11/1993 | Gianturco | |
| 5,282,829 A | 2/1994 | Hermes | |
| 5,290,299 A | 3/1994 | Fain et al. | |
| 5,306,234 A | 4/1994 | Johnson | |
| 5,309,927 A | 5/1994 | Welch | |
| 5,334,209 A | 8/1994 | Yoon | |
| 5,336,252 A | 8/1994 | Cohen | |
| 5,342,373 A | 8/1994 | Stefanchik et al. | |
| 5,366,459 A | 11/1994 | Yoon | |
| 5,409,499 A | 4/1995 | Yi | |
| 5,425,740 A | 6/1995 | Hutchinson | |
| 5,439,156 A | 8/1995 | Grant et al. | |
| 5,445,167 A | 8/1995 | Yoon et al. | |
| 5,452,733 A | 9/1995 | Sterman et al. | |
| 5,549,628 A | 8/1996 | Cooper et al. | |
| 5,582,616 A | 12/1996 | Bolduc et al. | |
| 5,609,599 A | 3/1997 | Levin | |
| 5,620,452 A | 4/1997 | Yoon | |
| 5,624,454 A | 4/1997 | Palti et al. | |
| 5,645,553 A | 7/1997 | Kolesa et al. | |
| 5,665,100 A | 9/1997 | Yoon | |
| 5,667,518 A | 9/1997 | Pannell | |
| 5,681,330 A | 10/1997 | Hughett et al. | |
| 5,683,405 A | 11/1997 | Yacoubian et al. | |
| 5,695,505 A | 12/1997 | Yoon | |
| 5,697,942 A | 12/1997 | Palti et al. | |
| 5,713,911 A | 2/1998 | Racenet et al. | |
| 5,758,420 A | 6/1998 | Schmidt et al. | |
| 5,782,397 A | 7/1998 | Koukline | |
| 5,782,844 A | 7/1998 | Yoon et al. | |
| 5,810,851 A | 9/1998 | Yoon | |
| 5,810,882 A | 9/1998 | Bolduc et al. | |
| 5,824,008 A | 10/1998 | Bolduc et al. | |
| 5,830,221 A | 11/1998 | Stein et al. | |
| 5,833,700 A | 11/1998 | Fogelberg et al. | |
| 5,843,121 A | 12/1998 | Yoon | |
| 5,893,863 A | 4/1999 | Yoon | |
| 5,919,202 A | 7/1999 | Yoon | |
| 5,921,991 A | 7/1999 | Whitehead et al. | |
| 5,921,996 A | 7/1999 | Sherman | |
| 5,921,997 A | 7/1999 | Fogelberg et al. | |
| 5,922,001 A | 7/1999 | Yoon | |
| 5,922,002 A | 7/1999 | Yoon | |
| 5,964,772 A | 10/1999 | Bolduc et al. | |
| 5,865,791 A | 11/1999 | Fleischman et al. | |
| 5,984,917 A * | 11/1999 | Fleischman et al. | 606/32 |
| 5,984,938 A | 11/1999 | Yoon | |
| 5,984,939 A | 11/1999 | Yoon | |
| 6,042,563 A | 3/2000 | Morejohn et al. | |
| 6,074,418 A | 6/2000 | Buchanan et al. | |
| 6,088,889 A | 7/2000 | Luther et al. | |
| 6,095,155 A | 8/2000 | Criscuolo | |
| 6,096,052 A | 8/2000 | Callister et al. | |
| 6,099,550 A | 8/2000 | Yoon | |
| 6,132,438 A | 10/2000 | Fleischman et al. | |
| 6,152,144 A * | 11/2000 | Lesh et al. | 128/898 |
| 6,165,183 A | 12/2000 | Kuehn et al. | |
| 6,193,732 B1 | 2/2001 | Frantzen et al. | |
| 6,231,561 B1 | 5/2001 | Frazier et al. | |
| 6,233,869 B1 | 5/2001 | Dearo | |
| 6,270,516 B1 | 8/2001 | Tanner et al. | |
| 6,280,415 B1 | 8/2001 | Johnson | |
| 6,290,674 B1 | 9/2001 | Roue et al. | |
| 6,296,656 B1 | 10/2001 | Bolduc et al. | |
| 6,299,612 B1 | 10/2001 | Ouchi | |
| 6,299,621 B1 | 10/2001 | Fogarty et al. | |
| 6,312,447 B1 | 11/2001 | Grimes | |
| 6,330,964 B1 | 12/2001 | Kayan et al. | |
| 6,379,366 B1 | 4/2002 | Fleischman et al. | |
| 6,387,105 B1 | 5/2002 | Gifford et al. | |
| 6,402,765 B1 | 6/2002 | Monassevitch et al. | |
| 6,416,554 B1 | 7/2002 | Alferness et al. | |
| 6,423,051 B1 | 7/2002 | Kaplan et al. | |
| 6,428,548 B1 | 8/2002 | Durgin et al. | |
| 6,436,088 B2 | 8/2002 | Frazier et al. | |
| 6,447,542 B1 | 9/2002 | Weadock | |
| 6,450,391 B1 | 9/2002 | Kayan et al. | |
| 6,485,407 B2 | 11/2002 | Alferness et al. | |
| 6,488,689 B1 | 12/2002 | Kaplan et al. | |
| 6,491,706 B1 | 12/2002 | Alferness et al. | |
| 6,506,149 B2 | 1/2003 | Peng et al. | |
| 6,508,829 B1 | 1/2003 | Levinson et al. | |
| 6,514,265 B2 | 2/2003 | Ho et al. | |
| 6,578,585 B1 | 6/2003 | Stachowski et al. | |
| 6,579,304 B1 | 6/2003 | Hart et al. | |
| 6,607,504 B2 | 8/2003 | Haarala et al. | |
| 6,607,542 B1 | 8/2003 | Wild | |
| 6,610,074 B2 | 8/2003 | Santilli | |
| 6,632,239 B2 | 10/2003 | Snyder et al. | |
| 6,652,515 B1 | 11/2003 | Maguire et al. | |
| 6,666,861 B1 | 12/2003 | Grabek | |
| 6,726,696 B1 | 4/2004 | Houser et al. | |
| 6,746,461 B2 | 6/2004 | Fry | |
| 6,793,664 B2 | 9/2004 | Mazzocchi et al. | |
| 6,849,075 B2 | 2/2005 | Bertolero et al. | |
| 6,849,078 B2 | 2/2005 | Durgin et al. | |
| 6,890,295 B2 * | 5/2005 | Michels et al. | 600/114 |
| 6,896,684 B2 | 5/2005 | Monassevitch et al. | |
| 6,911,032 B2 | 6/2005 | Jugenheimer et al. | |
| 6,960,218 B2 | 11/2005 | Rennich | |
| 7,077,862 B2 | 7/2006 | Vidlund et al. | |
| 7,217,284 B2 | 5/2007 | Houser et al. | |
| 7,645,285 B2 | 1/2010 | Cosgrove et al. | |
| 9,119,627 B2 | 9/2015 | Cosgrove et al. | |
| 2001/0005787 A1 | 6/2001 | Oz et al. | |
| 2001/0039434 A1 | 11/2001 | Frazier et al. | |
| 2001/0039435 A1 | 11/2001 | Roue et al. | |
| 2002/0010487 A1 | 1/2002 | Evans et al. | |
| 2002/0013605 A1 | 1/2002 | Bolduc et al. | |
| 2002/0022860 A1 | 2/2002 | Borillo et al. | |
| 2002/0026214 A1 | 2/2002 | Tanner et al. | |
| 2002/0026216 A1 | 2/2002 | Grimes | |
| 2002/0032454 A1 | 3/2002 | Durgin et al. | |
| 2002/0049457 A1 * | 4/2002 | Kaplan | A61B 17/12 606/139 |
| 2002/0055750 A1 | 5/2002 | Durgin et al. | |
| 2002/0058925 A1 | 5/2002 | Kaplan et al. | |
| 2002/0058967 A1 | 5/2002 | Jervis | |
| 2002/0062130 A1 | 5/2002 | Jugenheimer et al. | |
| 2002/0065524 A1 | 5/2002 | Miller et al. | |
| 2002/0072759 A1 | 6/2002 | Fry | |

(56) References Cited

U.S. PATENT DOCUMENTS

| | | |
|---|---|---|
| 2002/0077660 A1 | 6/2002 | Kayan et al. |
| 2002/0099390 A1 | 7/2002 | Kaplan |
| 2002/0103492 A1 | 8/2002 | Kaplan et al. |
| 2002/0111636 A1 | 8/2002 | Kaplan et al. |
| 2002/0111637 A1 | 8/2002 | Kaplan et al. |
| 2002/0111641 A1 | 8/2002 | Peterson et al. |
| 2002/0111647 A1 | 8/2002 | Khairkhahan et al. |
| 2002/0128640 A1 | 9/2002 | Swanson |
| 2002/0129822 A1 | 9/2002 | Furukawa et al. |
| 2002/0147456 A1 | 10/2002 | Diduch et al. |
| 2002/0169377 A1 | 11/2002 | Khairkhahan et al. |
| 2002/0177859 A1 | 11/2002 | Monassevitch et al. |
| 2002/0177862 A1 | 11/2002 | Aranyi et al. |
| 2003/0009441 A1 | 1/2003 | Holsten et al. |
| 2003/0018362 A1 | 1/2003 | Fellows et al. |
| 2003/0023141 A1 | 1/2003 | Stelzer et al. |
| 2003/0023248 A1 | 1/2003 | Parodi |
| 2003/0023266 A1 | 1/2003 | Borillo et al. |
| 2003/0036755 A1* | 2/2003 | Ginn ............................ 606/41 |
| 2003/0055422 A1 | 3/2003 | Lesh |
| 2003/0065339 A1 | 4/2003 | Snyder et al. |
| 2003/0158464 A1 | 8/2003 | Bertolero |
| 2003/0208209 A1* | 11/2003 | Gambale et al. ............ 606/144 |
| 2003/0220660 A1 | 11/2003 | Kortenbach et al. |
| 2003/0225442 A1 | 12/2003 | Kiran et al. |
| 2004/0010273 A1 | 1/2004 | Diduch et al. |
| 2004/0030335 A1* | 2/2004 | Zenati et al. ................... 606/51 |
| 2004/0049210 A1* | 3/2004 | VanTassel et al. ........... 606/151 |
| 2004/0073241 A1 | 4/2004 | Barry et al. |
| 2004/0097982 A1 | 5/2004 | Jugenheimer et al. |
| 2004/0215216 A1 | 10/2004 | Gannoe et al. |
| 2004/0220593 A1 | 11/2004 | Greenhalgh |
| 2005/0049681 A1 | 3/2005 | Greenhalgh et al. |
| 2005/0059987 A1 | 3/2005 | Hermann et al. |
| 2005/0085808 A1 | 4/2005 | Nakao |
| 2005/0149068 A1 | 7/2005 | Williams et al. |
| 2005/0149069 A1 | 7/2005 | Bertolero et al. |
| 2005/0277959 A1 | 12/2005 | Cosgrove et al. |
| 2006/0020271 A1 | 1/2006 | Stewart et al. |
| 2006/0178694 A1 | 8/2006 | Greenhalgh et al. |
| 2007/0129758 A1 | 6/2007 | Saadat |
| 2007/0213747 A1 | 9/2007 | Monassevitch et al. |
| 2008/0149685 A1 | 6/2008 | Smith et al. |
| 2008/0208324 A1 | 8/2008 | Glithero et al. |
| 2009/0012545 A1 | 1/2009 | Williamson et al. |
| 2010/0179570 A1 | 7/2010 | Privitera et al. |
| 2011/0009853 A1 | 1/2011 | Bertolero et al. |
| 2012/0035631 A1 | 2/2012 | Hughett et al. |
| 2012/0109161 A1 | 5/2012 | Privitera et al. |
| 2013/0237996 A1 | 9/2013 | Bertolero et al. |
| 2014/0012293 A1 | 1/2014 | Bertolero et al. |

FOREIGN PATENT DOCUMENTS

| | | |
|---|---|---|
| WO | WO 1998/018389 | 5/1998 |
| WO | WO 1999/011179 | 3/1999 |
| WO | WO 1999/062409 | 12/1999 |
| WO | WO 2001/035832 | 5/2001 |
| WO | WO 2001/197696 | 12/2001 |
| WO | WO 2003/011150 | 2/2003 |
| WO | WO 2003/096881 | 11/2003 |
| WO | WO 2005/060838 | 7/2005 |
| WO | WO 2007/009099 | 1/2007 |
| WO | WO 2010/011661 | 1/2010 |

OTHER PUBLICATIONS

Barry P. Rosenzweig et al., Thromboembolus from a Ligated Left Atrial Appendage, J Am Soc Echocardiography, vol. 14, pp. 396-398, May 2001.

Bassam O. Omari MD et al., Effect of Right Atrial Appendectomy on the Release of Atrial Natriuretic Hormone, The Journal of Thoracic and Cardiovascular Surgery, pp. 272-279, 1991.

Bruce D. Lindsay, MD, Obliteration of the Left Atrial Appendage: A Concept Worth Testing, The Society of Thoracic Surgeons, 1 pg., 1996.

C. Kaymaz et al., Location, Size and Morphological Characteristics of Left Atrial Thrombi as Assessed by Echocardiography in Patients with Rheumatic Mitral Valve Disease, Eur. J Echocardiography, vol. 2, pp. 270-276,. 2001.

C. Stollberger et al., Is Left Atrial Appendage Occlusion Useful for Prevention of Stroke or Embolism in Atrial Fibrillation?, Article, 4 pgs., 2002.

Claudia Stollberger MD et al., Elimination of the Left Atrial Appendage to Prevent Stroke or Embolism, Chest Journal, pp. 2356-2362, Dec. 2003.

Daniel C. Fisher et al., Large Gradient Across a Partially Ligated Left Atrial Appendage, Journal of the American Society of Echocardiography, vol. 11, No. 12, pp. 1163-1165, 1998.

David Lipkin et al., Aneurysmal Dilatation of Left Atrial Appendage Diagnosed by Cross Sectional Echocardiography and Surgical Removed, Article, 3 pgs., 1985.

Edward S. Katz MD et al., Surgical Left Atrial Appendage Ligation is Frequently Incomplete: A Transesophageal Echocardiograpic Study, Journal of the American College of Cardiolog, vol. 36, pp. 468-471, 2000.

Eugene Crystal et al., Left Atrial Appendage Occlusion Study (LAAOS): A randomized Clinical Trial of Left Atrial Appendage Occlusion During Routine Coronary Artery Bypass Graft Surgery for Long-Term Stroke Prevention, American Heart Journal, vol. 145, No. 1, pp. 174-178, Jan. 2003.

John A. Odell et al., Thoracoscopic Obliteration of the Left Atrial Appendage: Potential for Stroke Reduction?, The Society of Thoracis Surgeons, vol. 61, pp. 565-569, 1996.

John P. Veinot MD et al., Anatomy of the Normal Left Atrial Appendage, Article, pp. 3112-3115, 1997.

Jonathan L. Halperin et al., Obliteration of the Left Atrial Appendage for Prevention of Thromboembolism, Journal of the American College of Cardiology, pp. 1259-1261, 2003.

Joseph L. Blackshear MD et al., Appendage Obliteration to Reduce Stroke in Cardiac Surgical Patients with Atrial Fibrillation, Society of Thoracic Surgeons, vol. 61, pp. 755-758, 1996.

Joseph L. Blackshear MD et al., Thoracoscopic Extracardiac Obliteration of the Left Atrial Appendage for Stroke Risk Reduction in Atrial Fibrillation, Journal of the American College of Cardiology, 4 pgs., vol. 42, No. 7, 2003.

Joseph S. Coselli MD et al., Congenital Intrapericardial Aneurysmal Dilatation of the Left Atrial Appendage, The Annals of Thoracic Surgery, vol. 39, No. 5, pp. 466-468, May 1985.

K.I. Ganeshakrishnan et al., Congenital Intrapericardial Aneurysm of the Left Atrial Appendage, Thorac cardiovasc. Surgeon 40, pp. 382-384, 1992.

Laurence H. Coffin, Use of the Surgical Stapler to Obliterate the Left Atrial Appendage, Surgery, Gynecology & Obstetrics vol. 160, pp. 565-566, Jun. 1985.

Lawrence H. Cohn MD et al., Right Thoracotomy, Femorofemoral Bypass and Deep Hypotermia for Re-replacement of the Mitral Valve, Ann Thorac Surg, 3 pgs . . . . 1989.

M.T. Mole et al., Desmoid Tumour in Thoracotomy Scar 5 years After Excision of a Left Giant Atrial Appendage Aneurysm in Female With a Family History of Gardner's Syndrome, Thorac Cardiovasc Surgeon 40, pp. 300-302, 1992.

Miguel Angel Garcia-Fernandez et al., Role of Left Atrial Appendage Obliteration in Stroke Reduction in Patients with Mitral Alve Prosthesis, Journal of the American College of Cardiology, vol. 42, No. 7, pp. 1253-1258, 2003.

N.M. A-Saady et al., Left Atrial Appendage: Structure, Function, and Role in Thromboembolilsm, Article, pp. 547-554, 1999.

P. F. Grundeman et al., Experimental VideoThoracoscopic Cannulation of the Left Atrial Appendix, Surg. Endo. pp. 511-513, 1993.

R. Landymore et al., Staple Closure of the Left Atrial Appendage, The Canadian Journal of Surgery, vol. 27, No. 2, 2 pgs., 1984.

Redmond P. Burke et al., Improved Surgical Approach to Left Atrial Appendage Aneurysm, Journal of Cardiac Surgery, vol. 7, No. 2, pp. 104-107, 1992.

(56) References Cited

OTHER PUBLICATIONS

Tatsuya Hondo Md et al., The Role of the Left Atrial Appendage; A Volume Loading Study in Open-Chest Dogs, JPN Heart J, pp. 225-234, Mar. 1995.

Thomas V. Thomas MD, Left Atrial Appendage and Valve Replacement, Article, 2 pgs. undated.

Transesophageal Echocardiographic Correlates of Thromboembolism in High-Risk Patients with Nonvalvular Atrial Fibrillation, The American College of Physicians, pp. 639-647, Apr. 1998.

Verdi J. DiSesa et al., Ligation of the Left Atrial Appendage Using an Automatic Surgical Stapler, Division of Cardiac Surgery, Brigham and Women's Hospital, 3 pgs., 1988.

W. Dudley Johnson et al., The Left Atrial Appendage: Our Most Lethal Human Attachment! Surgical Implications, European Journal of Cardio-thoracic Surgery, 17 (2002), pp. 718-722.

\* cited by examiner

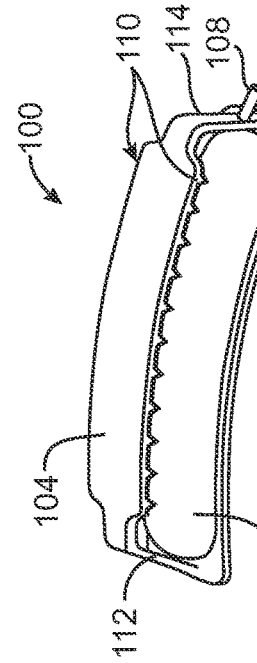
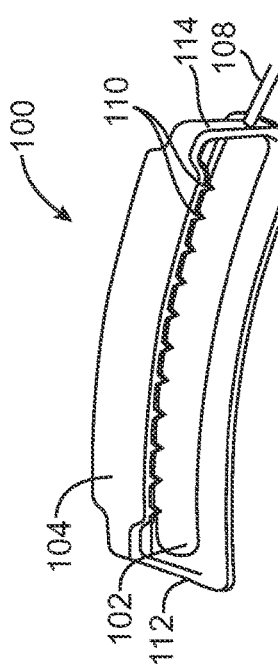
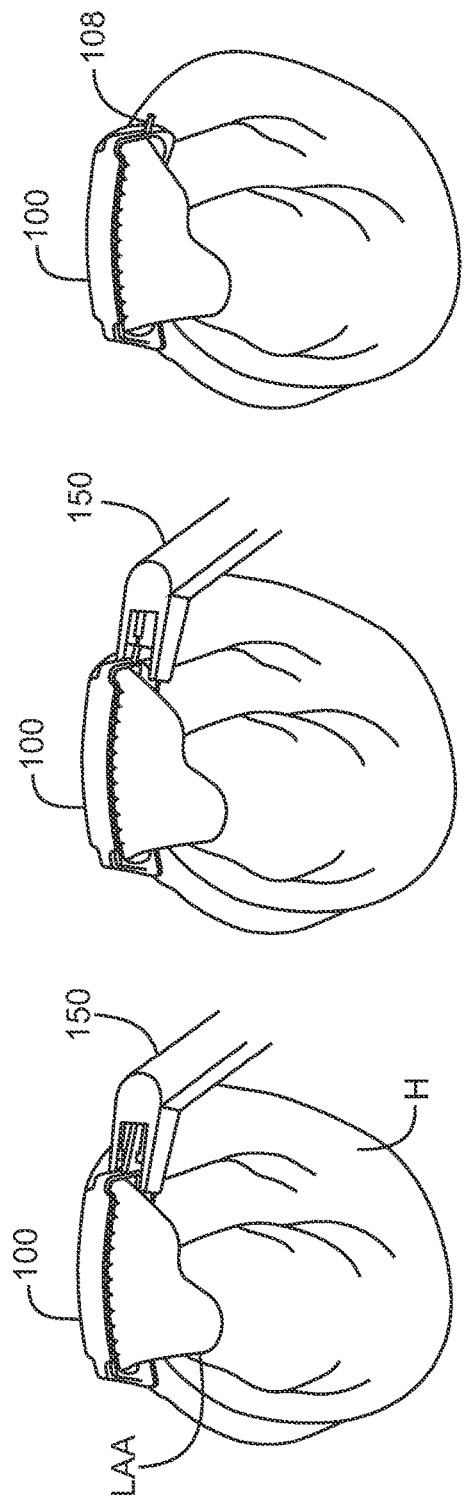

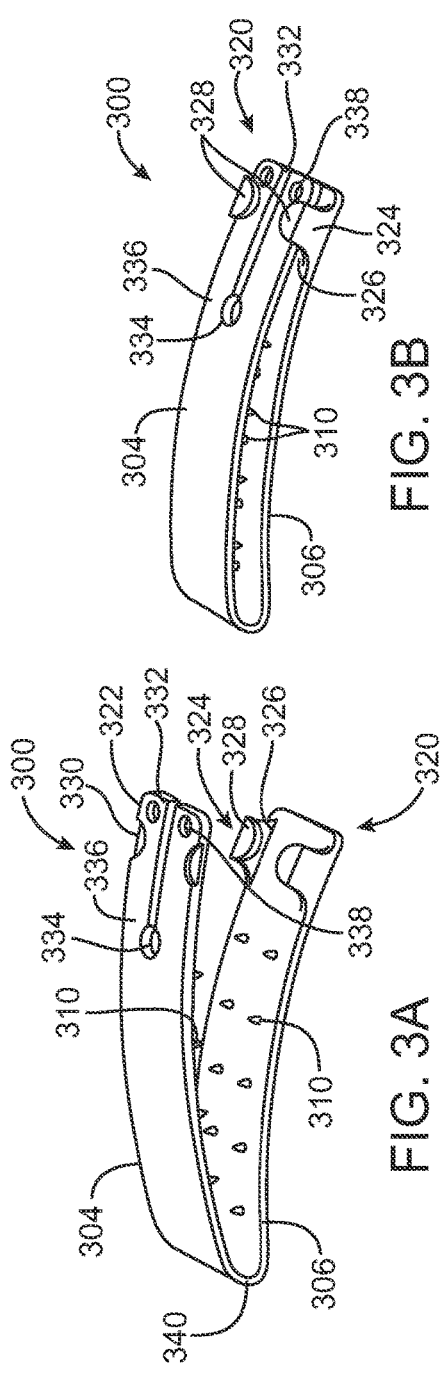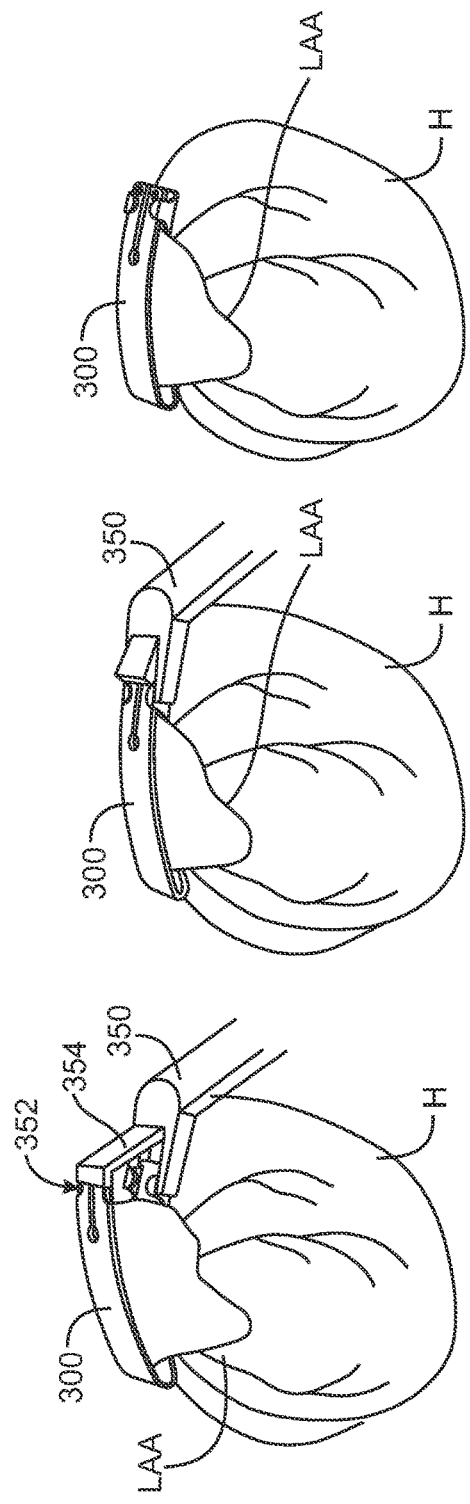

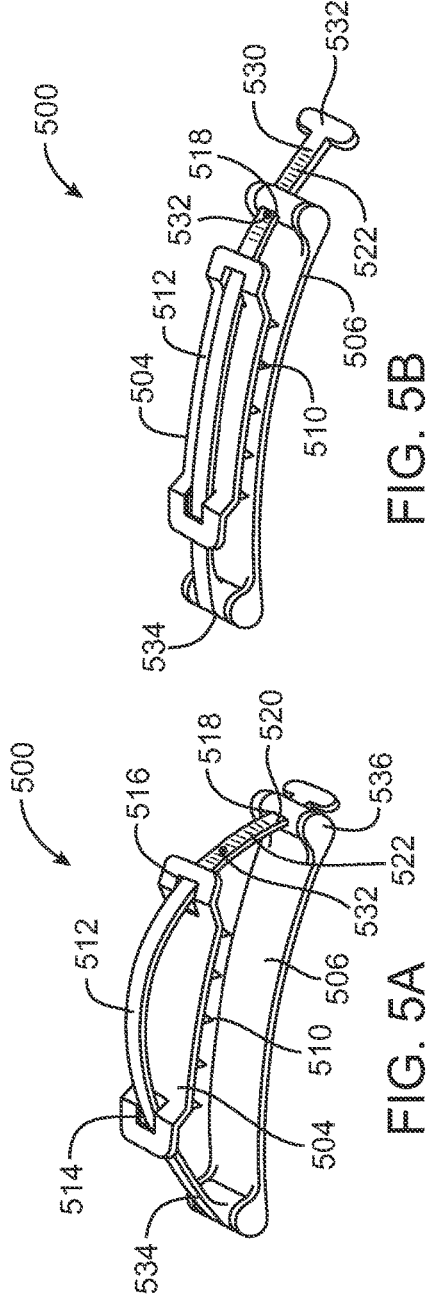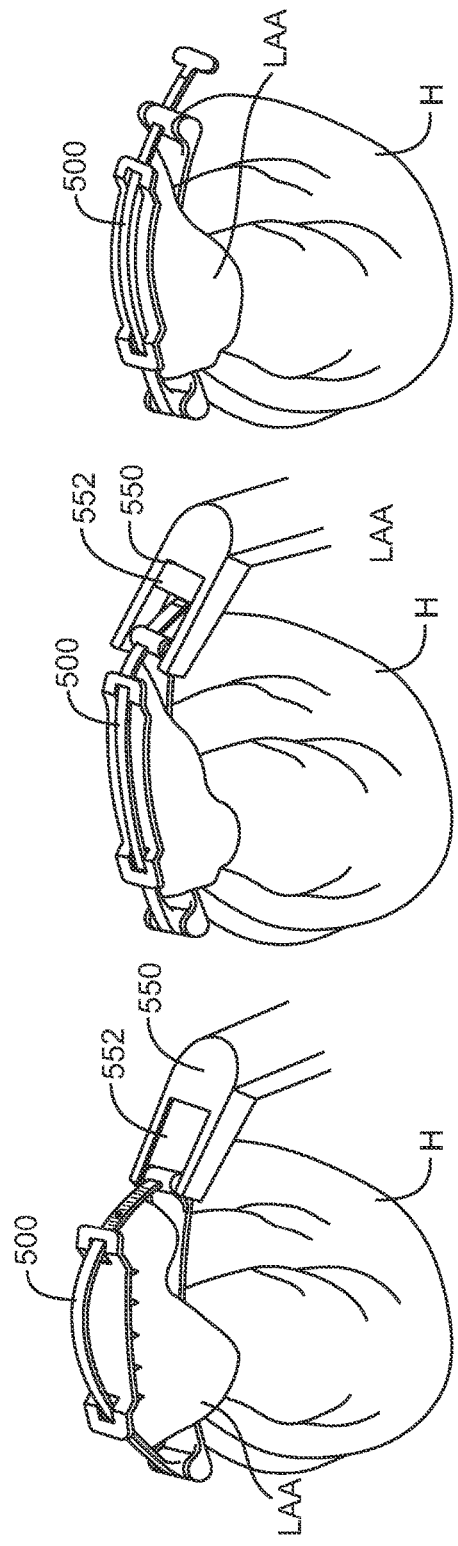

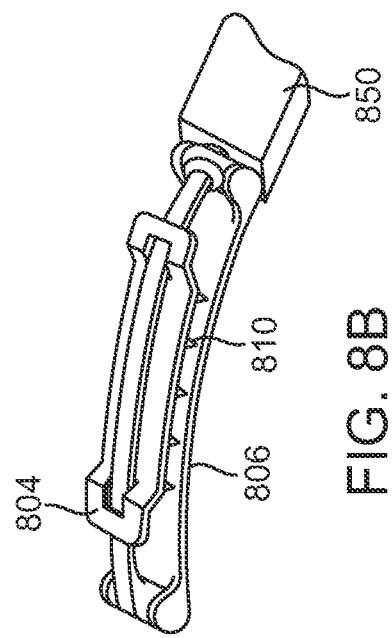
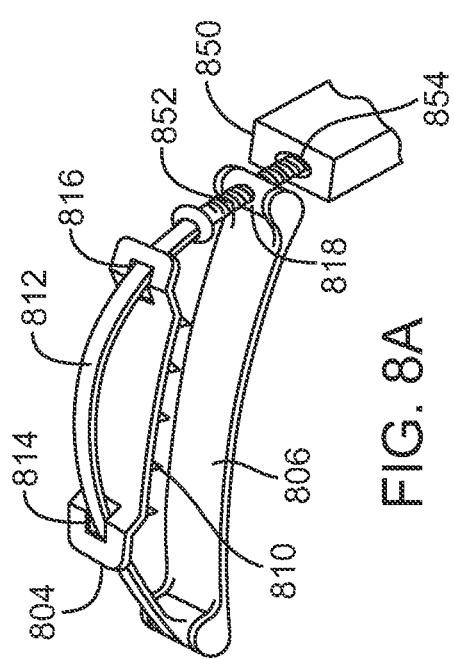

LEFT ATRIAL APPENDAGE DEVICES AND METHODS

CROSS-REFERENCES TO RELATED APPLICATIONS

This application is a divisional of application Ser. No. 10/988,003 filed Nov. 12, 2004 (now Abandoned), which is a non-provisional of and claims the benefit of priority to U.S. Provisional Patent Application Ser. No. 60/519,359, filed Nov. 11, 2003. U.S. application Ser. No. 10/988,003 is also a continuation-in-part of application Ser. No. 10/310,675 filed Dec. 4, 2002 (now U.S. Pat. No. 7,749,157 issued Jul. 6, 2010), which is a non-provisional of and claims the benefit of priority to U.S. Provisional Patent Application Ser. No. 60/337,070, filed Dec. 4, 2001. The entire contents of the above applications are hereby incorporated by reference in their entirety.

FIELD OF THE INVENTION

The present invention pertains to apparatus and methods for manipulating, positioning, clamping and stapling tissue. In particular it is a clamping device, which is particularly useful for treating the left atrial appendage of the heart to treat atrial fibrillation, but may also be useful for treatment of other tissues including the stomach, in gastric or bariatric surgery, or the lungs.

BACKGROUND OF THE INVENTION

Atrial fibrillation (AF) is a heart beat rhythm disorder (or "cardiac arrhythmia") in which the upper chambers of the heart known as the atria quiver rapidly instead of beating in a steady rhythm. This rapid quivering reduces the heart's ability to properly function as a pump. AF is characterized by circular waves of electrical impulses that travel across the atria in a continuous cycle. It is the most common clinical heart arrhythmia, affecting more than two million people in the United States and some six million people worldwide.

Atrial fibrillation typically increases the risk of acquiring a number of potentially deadly complications, including thrombo-embolic stroke, dilated cardiomyopathy and congestive heart failure. Quality of life is also impaired by common AF symptoms such as palpitations, chest pain, dyspnea, fatigue and dizziness. People with AF have, on average, a five-fold increase in morbidity and a two-fold increase in mortality compared to people with normal sinus rhythm. One of every six strokes in the U.S. (some 120,000 per year) occurs in patients with AF, and the condition is responsible for one-third of all hospitalizations related to cardiac rhythm disturbances (over 360,000 per year), resulting in billions of dollars in annual healthcare expenditures.

AF is the most common arrhythmia seen by physicians, and the prevalence of AF is growing rapidly as the population ages. As the prevalence of AF increases, so will the number of people who develop debilitating or life-threatening complications, such as stroke. According to Framingham Heart Study data, the stroke rate in AF patients increases from about 3% of those aged 50-59 to more than 7% of those aged 80 and over. AF is responsible up to 35% of the strokes that occur in people older than age 85.

Efforts to prevent stroke in AF patients have so far focused primarily on the use of anticoagulant and antiplatelet drugs, such as warfarin and aspirin. Long-term warfarin therapy is recommended for all AF patients with one or more stroke risk factors, including all patients over age 75. Studies have shown, however, that warfarin tends to be underprescribed for AF. Despite the fact that warfarin reduces stroke risk by 60% or more, only 40% of patients age 65-74 and 20% of patients over age 80 take the medication, and probably fewer than half are on the correct dosage. Patient compliance with warfarin is problematic, and the drug requires vigilant blood monitoring to reduce the risk of bleeding complications.

Electrophysiologists classify AF by the "three Ps": paroxysmal, persistent, or permanent. Paroxysmal AF—characterized by sporadic, usually self-limiting episodes lasting less than 48 hours—is the most amenable to treatment, while persistent or permanent AF is much more resistant to known therapies. Researchers now know that AF is a self-perpetuating disease and that abnormal atrial rhythms tend to initiate or trigger more abnormal rhythms. Thus, the more episodes a patient experiences and the longer the episodes last, the less chance of converting the heart to a persistent normal rhythm, regardless of the treatment method.

AF is characterized by circular waves of electrical impulses that travel across the atria in a continuous cycle, causing the upper chambers of the heart to quiver rapidly. At least six different locations in the atria have been identified where these waves can circulate, a finding that paved the way for maze-type ablation therapies. More recently, researchers have identified the pulmonary veins as perhaps the most common area where AF-triggering foci reside. Technologies designed to isolate the pulmonary veins or ablate specific pulmonary foci appear to be very promising and are the focus of much of the current research in catheter-based ablation techniques.

Although cardiac ablation devices and methods are currently available, many advances may still be made to provide improved devices and methods for ablating epicardial tissue to treat AF and other arrhythmias. For example, currently available devices can be difficult to position and secure on epicardial tissue to perform an ablation. Devices such as bipolar ablation clamps and others can ablate tissue only in very limited patterns, such as one or two straight lines. Ablation devices often have no means for shielding ablative energy, to avoid unwanted burning of tissues in the vicinity of the heart, such as the esophagus. Relatively few devices can be secured to epicardial tissue with sufficient force to allow for stabilization of the heart. And many ablation devices may not be introduced by minimally invasive means, thus requiring an open surgical procedure. Typically, therefore, current cardiac ablation procedures for AF treatment still require stopping the heart and using a cardiopulmonary bypass apparatus. Many of these shortcomings are addressed by devices and methods described in co-pending U.S. patent application Ser. No. 10/272,446, filed by the inventor of the present application on Oct. 15, 2002, the full disclosure of which is hereby incorporated by reference.

One possible mechanism for problems caused by AF is clots from the left atrial appendage embolizing and causing harm to the patient, such as a stroke. Therefore, one desirable procedure to prevent complications from AF is to prevent or reduce the likelihood of flow out of the left atrial appendage. Disclosed herein are methods and apparatus to treat tissue and are especially applicable to treatment of the left atrial appendage.

BRIEF SUMMARY OF THE INVENTION

In general, the present invention provides a device for manipulating and/or positioning tissue, such as clamping the left atrial appendage. Of particular interest is providing a device capable of bringing two tissue structures together. In one procedure, a clip applier may be used to apply one or more clips to the left atrial appendage of the heart to prevent clots from the left atrial appendage from embolizing and causing harm to the patient, such as a stroke. Clips are typically configured to segregate the left atrial appendage without severing the appendage, but otherwise any suitable configuration is contemplated. In one embodiment, clip applier may be used to simultaneously clip and excise the atrial appendage.

A basic version of the invention is a tissue clamping device or clip for altering the configuration of tissue including: a first elongated plate, a second elongated plate, a first connector connecting the ends of the first and second elongated plates, and a locking mechanism for locking the tissue clamping device in a closed position. The plates of the clip may be the same or different curvatures forming various shapes, including an opening with tapered ends, oval, ovoid, crescent, etc.

Another version of the invention includes an inflatable balloon or membrane located between two plates that are connected together at both ends. Rows of teeth may be located along the two edges of the opposing plate and are configured to extend beside one or both longitudinal edges of the balloon. For temporary installation, the balloon may be filed with a gas, saline or other fluid. For more permanent installation, the balloon may be filled with a material that will change phase over time, such as epoxy. In this case the balloon is filled and the epoxy is allowed to set. One or more applier devices may be used to place and actuate the inflatable balloon clip. The applier would include a fluid source in fluid communication with the balloon and a cutter and/or crimping tool to disconnect the balloon from the fluid source.

A further version of the invention includes a pair of flexible arms forming the end of one arm or plate of the clip to create the locking mechanism. The flexible arms fit within recesses in locking arms or posts extending from the opposing plate of the clip. To create a low profile a detent may be located in the flexible arms to allow the top of the locking arm to rest therein. One or more applier devices may be used to place and actuate the flexible arm clip. Projections on the applier may be set to engage openings in the flexible arms. Manipulation of the projections allows the flexible arms to be moved into the recesses to lock the clip in the closed position.

Yet a further version of the invention includes a cabled clip. This version has two plates and a cable. The cable extends from one end of the first plate, through a first cable opening in the first end of the second plate, through a second cable opening in the second end of the second plate, and through a third cable opening in the second end of the first plate. When the cable is pulled, it forces the plates into closer proximity, thereby clamping any tissue located therebetween. To hold the cable in place, teeth may extend from one or both sides of the cable. The teeth are configured to coordinate with one or more locking teeth in the third cable opening, thereby allowing the cable to move in only one direction through the opening. One or more applier devices may be used to place and actuate the cable clip. The applier device(s) may include a grip for holding the clip and a grip for holding the cable. While the clip is held, the cable is pulled. To prevent overcompression of the tissue a tension limiter may be used. The tension limiter may take the form of a weak point somewhere along the length of the cable, a limit on the amount of force a coordinating applier is capable of delivering, and/or a motion stop to prevent the cable motion or the plate motion. Other variations of the cable clip may use one or two worm gears on straight or inclined tracks to drive the motion of the cable.

Another version of the clip has two movable arms connected by a hinge. The hinge may be a pin hinge, living hinge or other pivot means. One or more applier devices may be used to place and actuate the flexible arm clip. The applier has a shaft and the arms of the clip are moveable with respect to the shaft. The applier and clip may be configured to move the arms and the corresponding tissue simultaneously, sequentially or to move only one of the two tissue structures.

The clips described above may be configured to enclosed a distal portion of the tissue to be clamped. Further, the clips may be configured to apply sufficient compression to the two tissue structures located in the clip, such that contact between the tissue structures is maintained under normal anatomical circulatory pressures of a patient. The arms or plates may be designed to apply approximately evenly distributed force or pressure along the length of the clip or alternately may be designed to apply greater force or pressure at one or more selected locations along the length of the clip. If desired, the clip may be closed or tightened in stages, such that after an initial amount of closure, the clip and/or tissue may be further adjusted prior to applying the full force to be eventually used. The device may also incorporate a mechanical or electrical/mechanical sensor that determines with adequate compression has been applied.

The motion of the clip and the associated motions of the applier, may be driven by any suitable mechanism, including but not limited to mechanical advantage, $CO_2$ pressure, vacuum pump, AC and/or DC power. The tissue may also be manipulated using an additional arm mounted on the clip, the clip applier or on a separate device. The additional arm may take the form of a probe, a grasping element, a vacuum source, a cutter and/or ablation device. These additional devices may be used before, during or after clip application.

Any of the above-indicated clips may also include any one or more options devices. Tissue engaging projections or fasteners, such as spikes, staples, rivets, sutures, and clips, may extending from one or both of the arms or plates. The tissue fasteners may be formed of a resilient, elastic or superelastic material. The tissue fasteners may be integrally formed with the arms of the clip, mounted within the clip or mounted within a cartridge that may be loaded into the clip. An alternate form of tissue attachment may be provided by a layer of adhesive on one or both arms of the clip. An energy source, such as RF or laser, may be used to treat or ablate the tissue near or within the clip. Clot detections devices may be mounted on the clip or on the applier and one or more needles may be used to withdrawn detected clots. A vacuum source may be connected to the needles to use suction to withdraw the clots. Additionally, the device may incorporate a sensor, such as UV, IR or electrical, that has the ability to determine electrical block and/or transmurality.

The tissue clamping device may be formed of a resilient material, thereby continuing to apply direct pressure to the tissue enclosed within the clip after the clip has been closed.

The tissue clamping device is used to alter the natural proximity of two tissue structures by displacing a first and second tissue structure with a tissue clamping device; bringing the first tissue structure into contact with the second tissue structure; and applying sufficient pressure with the tissue clamping device to the first and second tissue structures such that intimate contact between the first and second tissue structures is maintained under normal anatomical circulatory pressures of the cardiovascular system. The tissue clamping device may be used temporarily during surgery or it may be permanently applied. The clip and clip applier may be used directly or through another instrument, such as a visualization device, cannula or other surgical instrument. If used for treating the left atrial appendage, the tissue clamping device may be applied via a direct intercostal approach between the $4^{th}$ thru $6^{th}$ intercostals space.

BRIEF DESCRIPTION OF THE DRAWINGS

FIG. 1A shows a perspective view of a clip having an inflatable balloon;

FIG. 1B shows the clip of FIG. 1A with the balloon inflated;

FIGS. 2A-2C show the clip of FIG. 1A being applied to the left atrial appendage of a heart.

FIG. 3A shows a perspective view of a flexible arm clip having spikes and a low profile locking mechanism;

FIG. 3B shows the clip of FIG. 3A in the locked position;

FIGS. 4A-4C show the clip of FIG. 3A being applied to the left atrial appendage of a heart.

FIG. 5A shows a perspective view of a clip having a cable and plate configuration;

FIG. 5B shows the clip of FIG. 5A with the clip in the closed position;

FIGS. 6A-6C show the clip of FIG. 5A being applied to the left atrial appendage of a heart.

FIGS. 8A and 8B show a clip tension limiter.

DETAILED DESCRIPTION OF THE INVENTION

Figure 7A:
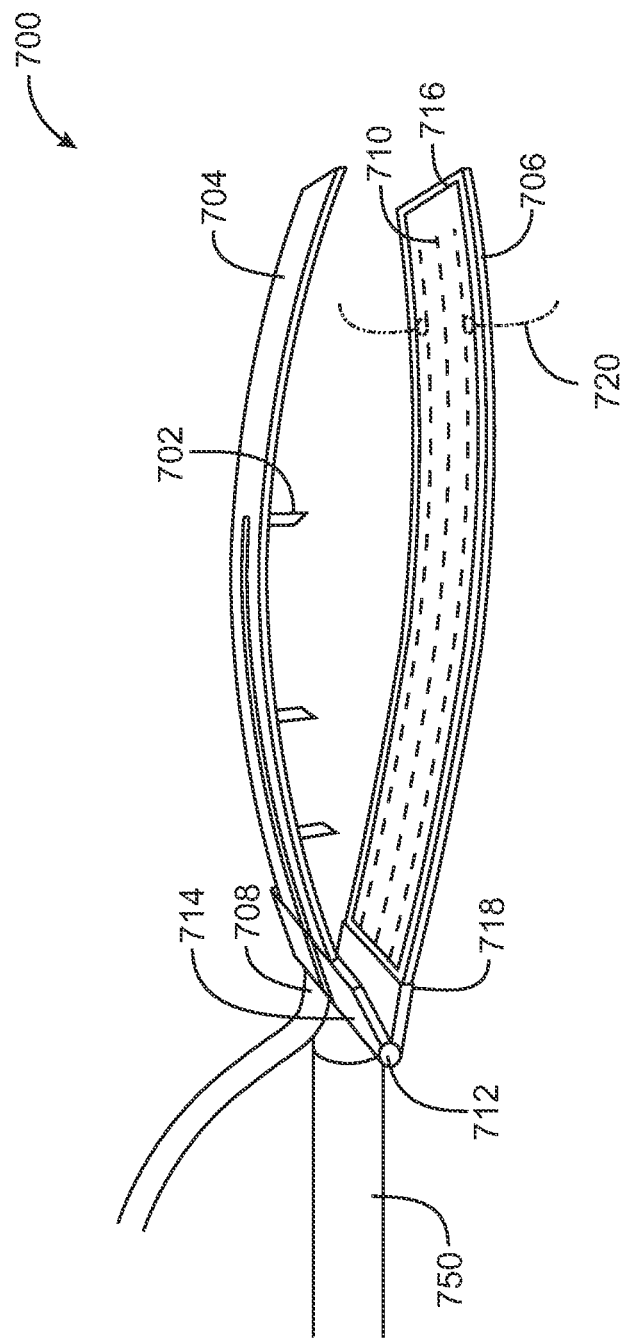
FIG. 7A is a perspective view of clip having needles for entering into the left atrial appendage and a suction lumen.

FIGS. 1A and 1B show perspective views of an inflatable clip 100 having a balloon 102 between the two plates 104, 106 forming the arms of the clip 100. FIG. 1A shows the inflatable clip 100 prior to inflation. In FIG. 1B, the balloon 102 has been inflated and the inflation tube 108 is has been crimped to provide permanent closure. In this embodiment, the top plate 104 of the inflatable clip 100 has one, two or more rows of traction tines or teeth 110 extending downward. The teeth 110 are located at or near the edge of the top plate 104 to allow the teeth 110 to puncture the left atrial appendage LAA on either side of the balloon 102 when the clip 100 is moved to the closed position. The balloon 102 is attached to the lower plate 106 of the inflatable clip 100. The balloon 102 extends along most or all of the length of the clip 100. The balloon 102 is sized and located such that as the balloon 102 inflates, the edges of the balloon 102 do not extend into the path of the teeth 110. The balloon 102 is inflated through a fill tube 108 extending from one end or side of the balloon 102 and out the end of the inflatable clip 100. If preferred, the orientation of the balloon 102 and teeth 110 may be reversed so that balloon 102 is attached to the top plate 104 and the teeth 110 extend from the lower plate 106.

FIGS. 2A-2C show the clip 100 of FIG. 1A being applied to the left atrial appendage LAA of a heart H. In FIG. 2A, a clip applier 150 is shown holding one end of the inflatable clip 100 to move the clip 100 over the end of the left atrial appendage LAA and to the base of the left atrial appendage LAA. In FIG. 2B, the balloon 102 has been inflated. If the clip 100 is being temporarily installed for use during a surgical procedure, the balloon 102 may be inflated with gas, saline or other liquid. Once the surgical procedure is complete, the saline may be removed to deflate the balloon 102 and allow removal of the clip 100. If the clip 110 is being used as a permanent or semi-permanent implant, the balloon 102 may be filled with saline, etc. or with a substance the sets, hardens or otherwise changes phase, such as epoxy. In this mode, the balloon 102 would be inflated with the epoxy. Once the epoxy had hardened, the inflation tube 108 may be crimped and cut with the clip applier 150 or other cutting tool. In FIG. 2C, the clip applier 150 has been removed and the inflatable clip 100 is permanently or semi-permanently attached to clamp the base of the left atrial appendage LAA. If necessary, the inflatable clip 100 may be removed by cutting one or both connector ends 112, 114, which extend between and connect the top plate 104 and the bottom plate 106. Once one or both of the connectors 112, 114 have been cut, the inflatable clip 100 may be removed.

FIGS. 3A and 3B show perspective views of a spiked, flexible arm clip 300. In FIG. 3A, the flexible arm clip 300 is in the open position in preparation for installation. In FIG. 3B, the flexible arm clip 300 is in the locked position. The flexible arm clip 300 has a top plate 304 and a bottom plate 306. Although spikes 310 may be located on the top plate 304, the bottom plate 306 or both top and bottom plates 304, 306, in the embodiment shown, spikes 310 are shown extending from both plates 304, 306. The spikes 310 are sized and configured to extend into the tissue being clamped to provide traction and inhibit unwanted motion of the clip 300 after installation. The closure mechanism 320 includes two arms 322 forming one end of the top plate 304, the two arms 322 are flexible such that they may be moved toward one another. The arms 322 are biased to remain straight. When the flexible arm clip 300 is in the closed position, the edges of the flexible arms 322 are located within recesses 326 created by locking arms 324. The locking arms 324 extend up from the bottom plate 306 and have a lateral extension forming the top 328 of the recess 326. If a low profile is desired, detents 330 may be cut into to the top surface of the top plate 304. In this case, when the clip 300 is in the locked position the lateral extensions 328 of the locking arms 324 rests in the detents 330. One version of the flexible arms 322 is created by a slot 332 extending in from one end of the top plate 304. At the end of the slot 332 is a circular opening 334. The narrowed section 336 of the top plate 304 adjacent the circular opening 334 creates a flexure point for the flexible arms 322 to bend. For ease of manipulation of the flexible arms 322, the ends of the arms 322 may have holes 338 extending partially or entirely therethrough.

An alternate version of this embodiment could utilize a single top arm without the flexible arms. In this case, movable locking arms could be moved to engage the edges of the top arm, thereby keeping the clip in the clamped or locked position. The detents may also be used with this embodiment to provide a low profile.

FIGS. 4A-4C show the clip 300 of FIG. 3A being applied to the left atrial appendage LAA of a heart H. In FIG. 4A, the flexible arm clip 300 is held by a clip applier 350. Two posts 352 on the clip applier 350 extend through the holes 338 in the ends of the flexible arms 322, thereby holding the arms 322 close together. The clip 300 is slid over the end of the left atrial appendage LAA and to the base thereof. Once in place, a hinged arm 354 of the clip applier 350 moves the top plate 304 of the clip 300 towards the bottom plate 306. As the clip 300 is closed, the spikes 310 pierce the tissue and the flexible arms 322 are lowered toward the locking arms 324. Once fully closed, the flexible arms 322 are released into place beneath the lateral extensions 328 of the locking arms 324, thereby holding the clip 300 in the closed position. Once closed, the clip applier 350 releases the clip 300 and the clip applier 350 is removed as seen in FIG. 4C.

If removal of the clip 300 is required, the flexible arms 322 of the top plate 304 of the clip 300 may be squeezed together, thereby removing them from beneath the lateral extension 328 of the locking arms 324. Once out of the recess 326, the clip 300 may be opened and removed. Alternately, the locking arms 324 may be cut to release the flexible arms 322 or the opposite end 340 of the clip 300, which connects the top plate 304 and the bottom plate 306, may be cut to separate the top plate 304 from the bottom plate 306.

FIGS. 5A and 5B show perspective views of a cable clip 500 in the open and closed position, respectively. The top plate 304 of the clip 500 has a plurality of optional spikes 510 extending down from the bottom surface thereof. A cable opening 514, 516 extends through the top plate 504 at or near either end of the top plate 504. A cable 512 or wire extends from the bottom plate 506 through the two cable openings 514, 516 in the top plate 504 and through a cable opening 518 in the bottom plate 506. In this version, the cable opening 518 in the bottom plate has one or more teeth 520 on one or both of the inside or outside wall. The cable 512 passing therethrough also has mating teeth 522, thereby allowing the cable 512 to move through the opening 518 in only one direction. Alternately, a ratchet device or other direction specific mechanism may be used.

To prevent excessive force being applied, a tension limiter 530 may be added to the device. The tension limiter may be created by forming a weak or frangible point 530 in the cable 512 designed to break when a preselected tension is reached or exceeded. A suitable location for the break point would be a location at or near the tab 532 at the end of the cable 512, preferably in a location which would have passed through the directional opening 518 prior to reaching the maximum tension. This would allow the clip 500 to maintain the maximum pressure after the tension is reached. If preferred, the frangible point 530 could be located along the main body of the cable 512, in order cause the cable 512 to be disabled if excessive force were reached. Alternately or in combination with the frangible point 530, a projection or stop 532 may extend from a preselected location on the cable 512 to limit the distance the cable 512 may be pulled. Other versions could utilize a rotational stop or penetration stop to prevent the distal end 534 of the cable 512 from rotating beyond a selected point or limiting how close together the top plate 504 and bottom plate 506 of the cable clip 500 could become. Another tension limiting option is to prevent the clip applier 550, seen in FIGS. 6A-6C, from applying excessive force. This may be accomplished by creating an electronic or mechanical limit to the force the applier 550 can apply. The sensor for detecting the force applied could be a mechanical sensor or electro-mechanical sensor.

FIGS. 6A-6C show the clip 500 of FIG. 5A being applied to the left atrial appendage LAA of a heart H. In FIG. 6A, one end of the bottom plate 506 of the cable clip 500 is held by a clip applier 550. For convenience, the end tab 532 of the cable 512 may be pre-engaged with a grip 552 of the applier 550. The cable clip 500 is slid over the end of the left atrial appendage LAA and to the base thereof. Once in place, the grip 552 pulls or grasps and pulls the cable 512 by the tab 532, thereby pressing the top plate 504 down towards the bottom plate 506 causing the spikes 510 to enter the upper surface of the tissue, as seen in FIG. 6B. If a directional opening 518 is used in the proximal end 536 of the clip 500, once the cable clip 500 is tighten or closed, the clip applier 550 releases the end of the bottom plate 506 and the clip applier 550 is removed as seen in FIG. 6C.

The cable clip 500 is especially well suited for situations where the clip 500 may need adjustment after partial installation on the tissue. For example, the cable clip 500 may be placed over the left atrial appendage LAA and slid toward the base thereof. Once, the coarse adjustment has been completed, the cable 512 is pulled a first amount to bring the top plate 504 into closer proximity to the tissue and the lower plate 506. Additional adjustment to the location of the clip 500 may be made at this point. Once in final position, the cable 512 is pulled further to bring the tissue into closer proximity and seal the left atrial appendage LAA. The initial amount may be selected such that the clip 500 surrounds, but does not engage the tissue. Alternatively, the amount may be selected to partially engage the tissue, but still allow the clip 500 to slide along the surface of the tissue. Similar actions may also be used with the other clips described herein to partially close the clip prior to providing the total force to be ultimately applied to the clip. Versions with no or short spikes or rounded projections may be well suited for this type of procedure.

FIG. 7A is a perspective view of clip 700 having needles 702 for entering into the left atrial appendage LAA and a suction lumen 708. This version of the clip 700 includes opposable arms 704, 706 connected with a hinge 712. The range of motion of the arms 704, 706 may be varied depending on the particular use of the clip 700. For example, for treatment of the left atrial appendage LAA, the range may be up to a 90-degree angle. The clip 700 could include a permanent or adjustable stop 714 to prevent the arms from being opened too far. The hinge 712 for the arms 704, 706 may be a living hinge, a pin hinge as shown, or other known hinge means. The example shown and described has two arms 704, 706. However, other this embodiment and the other versions could be used with additional arms or auxiliary devices. For example, an additional parallel, arm for stabilizing or manipulating the tissue during actuation of the device may be used. Furthermore, the clip 700 could be applied using one or more other standard or specialized devices. For example, the clip 700 could be mounted on a clip applier 750 and used with forceps or other devices using mechanical engagement or positive or negative pressure to manipulate, pierce, or otherwise treat or interact with the tissue.

The arms 704, 706 of the clip 700 may be selected to conform to the shape of the tissue to be clamped. For matching the shape of the left atrial appendage LAA, an ovoid or clam shape may be used, as seen in FIG. 7A. For matching the shape of the body of the heart H, similarly curved top and bottom arms are used, as seen in FIGS. 1A-6C. Matching the tissue shape promotes non-traumatic grasping. To further protect the tissue, a flexible sheet-like 716 element such as gauze or an adhesive film may be used between the arm 704, 706 and the tissue, thereby allowing the user to grasp tissue without damaging it.

The clip 704, 706 may be created with several different lengths and shapes of arms 704, 706 for different sizes and configurations of tissue and organs. Also, the arm length could be adjustable. For example, the arm 704, 706 could move along a sliding track 718 thereby moving the extending or shortening the length of the arms 704, 706, as seen in FIG. 7A. The adjustable length allows the clip 700 to vary the clamped or treated length according to the anatomy of the tissue being treated or the procedure being performed.

Any of the embodiments discussed herein may have one or more additional optional devices added to the arms or body of the device. These include, but are not limited to spikes, staples 710, rivets, sutures 720, tracks for the addition of other materials, drug therapies, RF ablation or treatment, laser ablation or treatment, needles 702, clot detection devices, actuation augmenting devices, etc. These optional devices are discuss in further detail below.

Figure 7B:
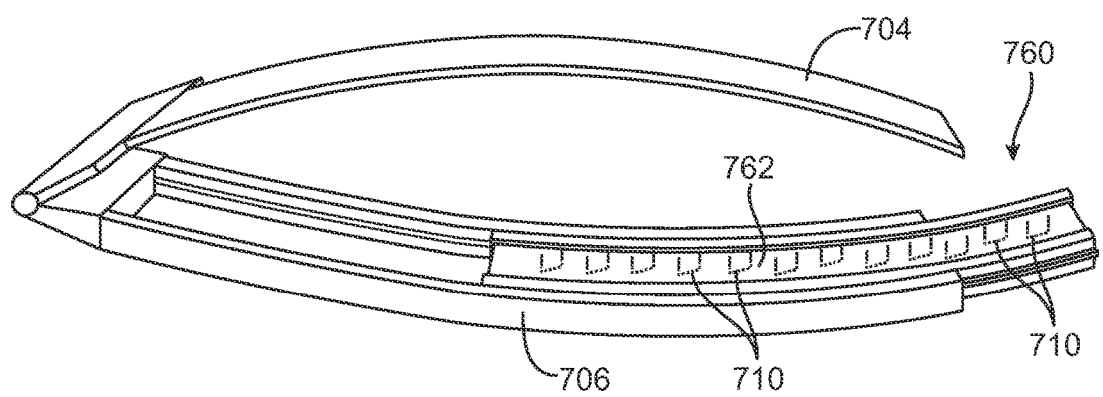
FIG. 7B is a perspective view of a clip have a replaceable cartridge.

The clip 700 may be used to staple tissue, in which case, one, two, three or more rows of staples 710 may be loaded into one or both arms 704, 706. The staples 710 may be loaded individually into openings in the arm 704, 706, or a replaceable or removable cartridge 760, seen in FIG. 7B, may be used to hold or load a set of staples 710. A plurality of different cartridges may be used having different numbers, configurations and lengths of staples 710. Each cartridge could also be optimized to provide specific staple patterns for different patients, different organs and/or organ specific needs. For example, wider and/or longer staples may be located toward the middle of the clip 700 to accommodate thicker tissue, while narrower and/or shorter staples 710 may be located toward the edges of the clip 700. Further, the staples 710 and other types of fasteners mounted to the arms 704, 706 may be configured with a length to penetrate only the outer surface of the tissue, through one tissue structure, through both tissue structures or through both tissue structures and engage the opposing arm 704, 706. For example, spikes may be designed to extend from both arms and each set designed to pierce approximately one tissue thickness. In this case the tips of the spikes would be close to or at the same level in the tissue. The spikes could be placed to pierce different locations of the tissue or, if designed to be at or short of full penetration, the spikes could be aligned. A staple type fastener could be designed to extend through both thickness of the tissue and extend into or through openings in the opposing arm of the clip. The staple ends could then be manually or automatically bent over or otherwise manipulated to engage the opposing arm. The openings in the arm could be formed by the staple ends piercing the arm, or the openings may be preformed to align with and bend the staple ends.

A track, adhesive 716 or other permanent or temporary attachment may be added or used to connect a scaffold, wire mesh, sealing strip, pericardium, DACRON or other material to one or both arms of any of the versions of the clip device. If used with the staples 710, the staples could pierce both the material and the tissue, thereby stapling the material thereto. A simple form could use longitudinal grooves near the edges of the device arms into which a semi-rigid material may be slid. If a more flexible material is used, a cartridge attachment 760, seen in FIG. 7B, may be attachable to the inside face of the arm 706. The cartridge 760 would automatically or manually release the sheet of material 762 when the clamp was actuated. Alternately, a flexible material could be temporarily clamped to the arm of the device. The additional material may be used to improve many characteristics including, but not limited to load bearing, stability, sealing and/or healing of the tissue being treated. Alternate versions could also be used to apply one time or time-release drug therapies, which could have anti-clotting, antibiotic, healing or other properties. In the one-time dose versions, the material need not be connected to the tissue. The material could remain in place attached to the arm as long as the device was attached the tissue and would be removed along with the device once treatment was complete. In other versions, an adhesive or other attachment could connect the material to either or both of the tissue structures. The adhesive could be used with or in place of the other fasteners described herein, such as spikes, staples, rivets, sutures, etc.

A mechanism for RF treatment or ablation may be added to one or both arms to treat or ablate the tissue around the treatment site. Similarly, a laser source could be added to treat or ablate tissue. In one embodiment, an integrated linear laser would be activated from the handle to deliver treatment or ablation to the tissue. The delivery could be through the clip or the delivery device.

Fixed or retractable needles 702 may be added to one or both arms 704, 706. The needles 702 may be used to inject drug therapies and/or be attached to a suction lumen 708 to remove clots. Additionally, the needle 702 may be used to monitor the formation or presence of clots to determine whether or not suction removal of the clot(s) is necessary. An example of these needles 702 is shown in FIG. 7A.

The arms 704, 706 may be actuated by many different mechanisms, including a trigger in a pistol grip, a syringe grip, a scissors grip, etc. The manual force applied to the handle may be augmented to reduce the gripping action required to drive the staples and/or arm movement. The augmenting force may be proved by $CO_2$ pressure, vacuum pump, etc. Power to these devices may be alternating current or battery power.

FIGS. 8A and 8B show a clip 800 having a different version of a tension limiter using a threaded rod 854 as an actuation mechanism. One end of the bottom plate 806 of the clip 800 is held by a clip applier 850. A cable 812 is located over the top plate 804 of the clip 800 and through holes 814, 816, 818 passing through the part of the clip 800. The end of the cable 812 is threaded 852 to engage the threaded rod 854 located within the clip applier 850. The clip 800 is slid over the end of the left atrial appendage LAA and to the base thereof. Once in place, the threaded rod 854 is twisted to pull the end of the cable 812, thereby pressing the top plate 804 down towards the bottom plate 806 causing the spikes 810 to enter the upper surface of the tissue. The torque or twisting force applied to the threaded rod will dictate the amount of compressive force the clip applies. A torque reading may be shown to the user to indicate the amount of force or the system could use a built in limit beyond which, the applier would not continue to twist the rod. Various mechanisms may be used to secure the cable 812 for permanent installation of the clip 800. For example, the nut or other twist on fastener may be associated with the worm gear 854 and left in place, or an adhesive may be used to permanently fix the end of the cable 812, etc.

Figure 9A:
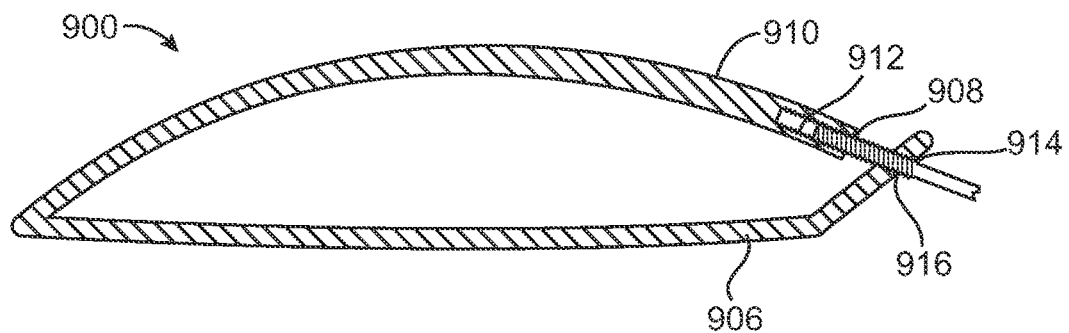
FIGS. 9A and 9B show clips using a worm gear as an actuation mechanism.
Figure 9B:
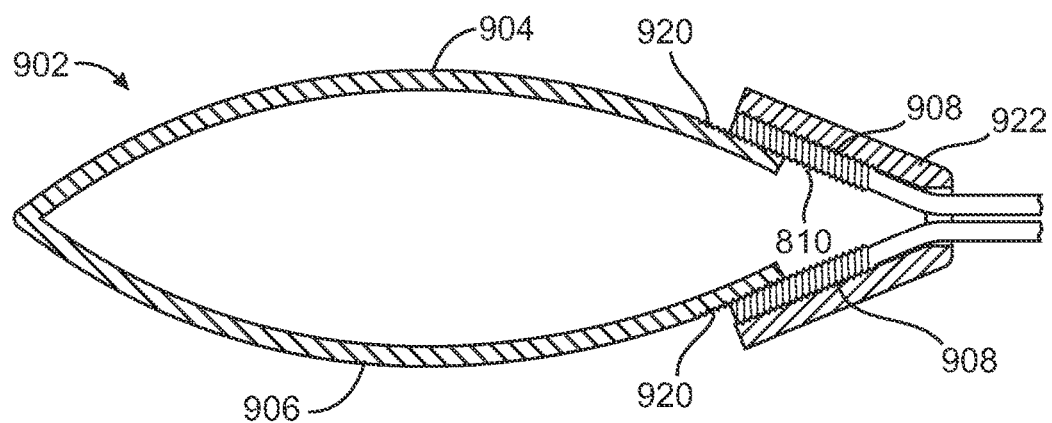

FIGS. 9A and 9B show clips using worm gears as actuation mechanisms. In FIG. 9A, a single threaded rod 908 is twisted to pull the top arm 904 down toward the bottom arm 906. Once in the clip 900 is closed, the threaded rod 908 may be glued or otherwise locked into place to hold the clip 900 in the closed position. Alternately, the friction of the threaded rod 908 against the grooves 910 in the opening 912 of the top arm 904 and the grooves 914 in the opening 916 of the bottom arm 906 may be sufficient to hold the clip 900 closed. In FIG. 9B, both the top arm 904 and the bottom arm 906 each have a set of grooves 920 located on the outside surface. A V-shaped endcap 922 is placed over the ends of the arms 904, 906. A threaded rod 908 within each side of the endcap 922 pulls the ends of the clip 902 together, thereby compressing the tissue located within the clip 902. When close, an adhesive may be used to lock the parts in place, or any other suitable locking mechanism may be used, if needed.

A rivet may be used as the connector to hold together the top and bottom arms of any of the embodiments of the clip discussed herein. The rivet could be used as the connector only or it may be used to provide closing pressure.

Several of the embodiments described herein use mechanical motion to provide pressure or force to the tissue being treated. In addition to or instead of the mechanical force, any of the clips described herein may be formed of a resilient material, such as NITINOL or other superelastic or elastic material. Using a resilient material allows the clip to be pre-stressed, such that when the clip is closed, the residual forces in the clip material continue to provide active pressure on the tissue within the clip.

Further embodiments may use mechanisms that connect both ends of the clip after two separate pieces are located in place around the tissue to be treated. Once in place, a latching or locking mechanism may engage one end, then the second end, or the two ends may be connected simultaneously.

Another version of the clip would be preloaded or stressed. In this version, the clip is made of a resilient material and preformed in the closed position. For installation, the clip would be deformed to allow the user to place the clip over the tissue. When the clip is released, the clip would return to the closed position, conforming to the shape of the tissue and clamping, compressing or otherwise manipulating the tissue.

When one or more of the clips is used to treat the left atrial appendage LAA, the procedure may be done during full open heart surgery or during minimally invasive surgery. A possible direct approach to the left atrial appendage during a minimally invasive procedure would be an intercostal approach between the ribs, in particular an approach between the $4^{th}$ thru $6^{th}$ intercostals space. Further, the clip and clip applier may be introduced via a visualization device.

In some procedures, one or more additional devices may be introduced into patient as a part of the clip applier or in addition to the applier. These include devices such as a visualization device, positioning or ablation device, such as one or more of the devices described in U.S. patent application Ser. No. 10/272,446, which has been previously incorporated by reference. The present invention and the auxiliary devices may be introduced into the patient via a primary incision placed in any suitable location. For example, in one embodiment the primary incision comprises a subzyphoid incision, but in other embodiments a subcostal incision, an intercostal incision or any other suitable incision may be used. To facilitate introduction of visualization device, one or more retractors may be used to increase the size of an incision. One or more additional incisions on patient may include, for example, an arterial/venous access incision for providing access for a perfusion cannula to a cardiopulmonary bypass machine or for any other device, an incision for a separately-introduced left atrial appendage clamp or clip, and/or a femoral incision for providing access to a femoral artery for entry of a mapping catheter or any other device. Any suitable combination of incisions and devices is contemplated within the scope of the invention.

Several versions of device applicators are disclosed herein, these may be configured to partially or completely release once in place over the tissue to be treated. If this is the case an additional tool may be used to move the device between the open and the clamped or closed position. Releasing or decoupling the device from the applicator avoids translation or magnified translation of motion caused by dissimilar motions between the moving operator and moving tissue structure, minimizing trauma to the tissue structure to be altered.

The actuation of the embodiments may be set to move two arms simultaneously to move two tissue structures together simultaneously or the arms may be moved separately such that the majority of the motion is provided by one arm and the associated tissue moving towards the second tissue and corresponding arm. The pressure or force applied to the tissue may be used bring two tissues closer together, to seal an opening or to cut through and remove a portion of the tissue.

In each of these cases described for treating the left atrial appendage, the force applied to the tissue should be sufficient pressure or force to create and maintain contact between the top and bottom tissue structures of the left atrial appendage and to prevent the passage of fluid therethrough during pressures up to and/or slightly above normal anatomical circulatory pressure. Once sealed, the appendage may be left in place or may be partially or completely removed by ablation or dissection.

Each of the clips described herein are designed to enclose the distal end of the at least one tissue structure prior to application of forces between device and tissue. Further, the clips may be designed to apply relatively even distribution of force along the longitudinal axis of the tissue that is in contact with the clip. In some cases, it may be desirable to have one or more higher pressure area(s). In these cases, the clip would be configured such that a larger force would be exerted at a chosen location(s) along the length of the clip.

Many features have been listed with particular configurations, options, and embodiments. Any one or more of the features described may be added to or combined with any of the other embodiments or other standard devices to create alternate combinations and embodiments.

Although the invention has been fully described above, in relation to various exemplary embodiments, various additions or other changes may be made to the described embodiments without departing from the scope of the present invention. Thus, the foregoing description has been provided for exemplary purposes only and should not be interpreted to limit the scope of the invention as set forth in the following claims.

What is claimed is:

1. A method of segregating an atrial appendage of a patient with an atrial segregation device during a cardiac surgical treatment, the method comprising:
   delivering the atrial segregation device to the atrial appendage of the patient using an applier device, wherein the atrial segregation device comprises a biocompatible material, the atrial segregation device comprising a first arm extending parallel to a second arm where the first arm and second arm are joined at first and second ends of the atrial segregation device such that the atrial segregation device is slid over the atrial appendage while connected to the applier device;
   compressing the first and second arms of the atrial segregation device onto the atrial appendage by moving the first arm towards the second arm using the applier device while the atrial segregation device is engaged with the applier device; and
   segregating the atrial appendage of the patient with the atrial segregation device and releasing the atrial segregation device from the applier device.

2. The method of claim 1, wherein the atrial segregation device is left in place after surgery.

3. The method of claim 1, wherein the atrial segregation device is applied under direct visualization.

4. The method of claim 1, wherein the atrial segregation device is applied via a direct intercostal approach between ribs of a patient.

5. The method of claim 1, wherein the atrial segregation device is applied via a direct intercostal approach between the 4th through 6th intercostal spaces.

6. The method of claim 1, wherein a tissue region adjacent to the atrial segregation device is dissected distal to the atrial segregation device.

7. The method of claim 1, further comprising:
manipulating the atrial appendage between the first arm and second arm of the atrial segregation device.

8. The method of claim 7, wherein manipulating the atrial appendage is performed by suction.

9. The method of claim 1, further comprising using suction during delivering the atrial segregation device to the atrial appendage.

10. The method of claim 9, wherein the suction is applied with the use of a separate suction device.

11. The method claim of 1, wherein the atrial segregation device comprises a superelastic material.

12. The method of claim 1, further comprising:
applying at least one staple to maintain a pressure on the atrial appendage.

13. The method of claim 1, further comprising applying at least one rivet to the atrial appendage.

14. The method of claim 1, further comprising applying at least one suture to maintain a pressure on the atrial appendage.

15. The method of claim 1, further comprising applying RF energy to the atrial appendage.

16. The method of claim 1, further comprising applying an adhesive to the atrial appendage.

17. The method of claim 16, wherein applying the adhesive comprises applying the adhesive on at least one elongated plate of the atrial segregation device.

18. The method of claim 1, further comprising:
applying laser energy to the tissue to maintain segregating the atrial appendage.

19. The method of claim 1, wherein compressing the first and second arms of the atrial segregation device onto the atrial appendage comprises displacing two portions of the atrial appendage simultaneously.

20. The method of claim 1, wherein compressing the atrial segregation device onto the atrial appendage comprises displacing two portions of the atrial appendage sequentially.

21. The method of claim 1, wherein:
the first and second arms of the atrial segregation device comprise opposing surfaces of a size and shape to engage opposite sides of the atrial appendage;

each of the opposing surfaces includes a plurality of teeth; and applying pressure with the atrial segregation device comprises engaging the teeth with the outer surfaces of the atrial appendage.

22. The method of claim 21, further comprising locking the atrial segregation device in a closed position.

23. The method of claim 1, wherein the atrial appendage is positioned external to an atrium to which the atrial appendage is attached.

24. The method of claim 1, wherein compressing the first and second arms of the atrial segregation device onto the atrial appendage comprises using a clamp on the applier device to exert pressure to close the atrial segregation device.

25. The method of claim 1, further comprising locking the first and second arms at the second end of the atrial segregation device comprises limiting a tension in the atrial segregation device to prevent application of an excessive force while segregating the atrial appendage.

* * * * *